(12) United States Patent
Dutta et al.

(10) Patent No.: US 9,170,225 B2
(45) Date of Patent: Oct. 27, 2015

(54) OBTAINING SELECTIVITY IN GAS SENSORS VIA A SENSOR ARRAY SYSTEM COMPOSED OF P AND N TYPE MATERIAL

(71) Applicants: The Ohio State University, Columbus, OH (US); Solomon Ssenyange, Fremont, CA (US)

(72) Inventors: Prabir Dutta, Worthington, OH (US); Suvra Mondal, West Bengal (IN); Solomon Ssenyange, Fremont, CA (US)

(73) Assignee: Ohio State Innovation Foundation, Columbus, OH (US)

( * ) Notice: Subject to any disclaimer, the term of this patent is extended or adjusted under 35 U.S.C. 154(b) by 298 days.

(21) Appl. No.: 13/780,906

(22) Filed: Feb. 28, 2013

(65) Prior Publication Data
US 2013/0219995 A1  Aug. 29, 2013

Related U.S. Application Data

(60) Provisional application No. 61/604,752, filed on Feb. 29, 2012.

(51) Int. Cl.
*G01N 27/04* (2006.01)
*G01N 27/12* (2006.01)
*G01N 33/497* (2006.01)

(52) U.S. Cl.
CPC .............. *G01N 27/04* (2013.01); *G01N 27/129* (2013.01); *G01N 33/497* (2013.01)

(58) Field of Classification Search
CPC .... G01N 27/04; G01N 27/129; G01N 33/497
See application file for complete search history.

(56) References Cited

U.S. PATENT DOCUMENTS

2003/0089899 A1*  5/2003  Lieber et al. ........................ 257/9

* cited by examiner

*Primary Examiner* — Laura Martin
*Assistant Examiner* — Alex Devito
(74) *Attorney, Agent, or Firm* — Muenier Carlin & Curfman LLC

(57) ABSTRACT

Systems and methods for discriminating among volatile compounds is provided using a semiconductor junction structure or sensor device. Sensor devices of the present disclosure employ a combination of hole carriers (p-type) and electron carriers (n-type) metal oxides deposited, for example, on a gold microspring array designed so that it has several leads that are at different distances from each other.

17 Claims, 7 Drawing Sheets

OBTAINING SELECTIVITY IN GAS SENSORS VIA A SENSOR ARRAY SYSTEM COMPOSED OF P AND N TYPE MATERIAL

CROSS-REFERENCE TO RELATED APPLICATIONS

This Non-Provisional Patent Application claims the benefit of the filing date of U.S. Provisional Patent Application Ser. No. 61/604,752, filed Feb. 29, 2012, entitled "OBTAINING SELECTIVITY IN GAS SENSORS VIA A SENSOR ARRAY SYSTEM COMPOSED OF P AND N TYPE MATERIAL," the teachings of which are herein incorporated by reference.

BACKGROUND

The present disclosure relates to sensor arrays. More particularly, it relates to sensor arrays for sensing and identifying analytes, for example identifying an ambient gas.

Sensor arrays find extensive use in electronic noses for detection of a large variety of volatile compounds. Typically, these sensor arrays consist of a finite number of sensors (e.g., ~10) with each sensor producing a slightly different response to the analyte (or mixture of analytes). Often the arrays are based on measuring resistance, and materials for the sensor array include, for example, metals, metal oxides, and/or polymers. Metal oxide semiconductors (MOS)-based sensors (n-type: $SnO_2$, $ZnO_2$, $TiO_2$, $WO_3$, etc.; p-type: $CuO$, $TeO_2$, etc.) may be used to detect volatile compounds (such as acetone, propanol, ethanol) or toxic gases (such as $CO$, $NO$, $NO_2$, etc). In general terms, MOS sensors incorporate a sensing layer formed of material selected for a targeted gas. When the targeted gas interfaces with the sensing layer material, the target gas molecules are adsorbed and react on the crystal surface, resulting in a change in conductivity of the sensing layer. By measuring the change in conductivity (e.g., resistivity), the presence and amount (often in ppm or ppb) of the targeted gas (or other compound or analyte of interest) can be estimated. Sensitivity/selectivity to a particular gas depends on the intrinsic properties of the MOS material, and can be modulated by doping to alter the electrical properties or by introducing catalysts such as Au, Pt, Pd to alter the chemical properties. Operating temperature is also a key parameter to optimize sensitivity.

Cross sensitivity to interfering gases is an issue of MOS based sensor devices that remains unresolved. Many strategies have been reported to reduce interferences, including the use of catalysts, and adsorptive or catalytic filters.

SUMMARY

Some aspects of the present disclosure relate to a sensor system for determining presence of an analyte in a sample gas. The sensor system includes a sensing element, a plurality of electrode wires and a controller. The sensing element includes a p-type MOS material and an n-type MOS material. The p-type MOS material is arranged adjacent to and contacts the n-type MOS material at a diffuse p-n junction. The electrode wires include a first electrode wire connecting spaced electrodes in the p-type MOS material. A second electrode wire connects spaced electrodes in the n-type material, and a third electrode wire connects an electrode in the p-type MOS material with an electrode in the n-type MOS material. The controller (e.g., a computer programmed or loaded with software) is programmed to determine a measured resistance across each of the first-third electrodes when the sensing element is exposed to a sample gas. The controller is further programmed to estimate a null point from the measured resistances and identify a sample gas based on a statistical comparison of the measured resistances with a calibration database.

BRIEF DESCRIPTION OF THE DRAWINGS

In the accompanying drawings which are incorporated in and constitute a part of the specification, embodiments of the disclosure are illustrated, which, together with a general description given above, and the detailed description given below, serve to exemplify the embodiments of this disclosure.

DETAILED DESCRIPTION

Figure 1:
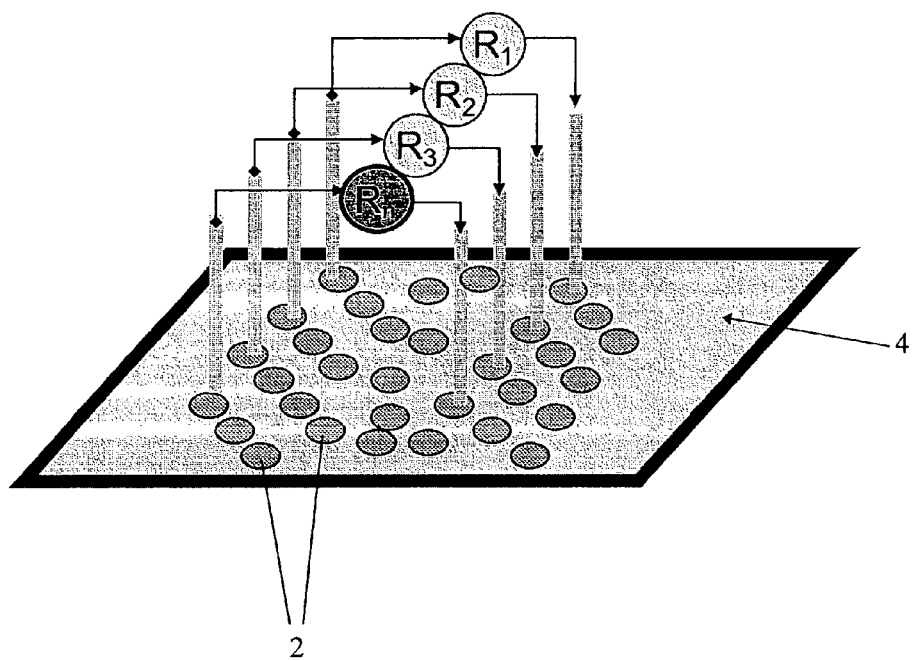
FIG. 1 illustrates a schematic representation of a sensing element on a platform in accordance with one embodiment of an apparatus in accordance with principles of the present disclosure.

With reference to FIG. 1, a sensor or sensing element 2 (e.g., a single sensor) on a suitable platform 4 is contemplated. In one embodiment, multiple measurements $R_1$, $R_2$, $R_3$ are taken of some electrical property across various parts of the same sensor 2. For example, the sensing element could be metal oxide particles, gold particles with surface modifications, etc. $R_1$, $R_2$, $R_3$, $R_n$ are the resistances measured upon exposure to gas or other analyte. Different analytes adsorb differently on the sensing element 2. Therefore, a pattern of the measured resistances $R_1$-$R_n$ would change as a function of the analyte being sensed. These patterns can be distinguished by statistical methods, such as principal component analysis and neural networks programmed into a computer or controller or logic device (not shown) that receives and interprets the measured resistances $R_1$-$R_n$. One advantage of such a sensor system (e.g., the sensor 2 and the controller) is that hundreds of resistance values can be obtained for each sample without resorting to ~100 different sensors. Selectivity and sensitivity can be modulated (e.g., by the controller) by changing the nature of the sensing element aiming for high orthogonality. The platform 4 can be maintained at a temperature that is optimized for the analyte. Such sensor arrays find applications in industrial, consumer, and biomedical applications.

In some embodiments of the present disclosure, a novel approach to discriminate among volatile compounds is provided using a semiconductor junction structure or sensor device. As discussed in more detail below, sensor devices of the present disclosure employ a combination of hole carriers (p-type) and electron carriers (n-type) metal oxides deposited, for example, on a gold microspring array designed so that it has several leads that are at different distances from each other.

Figure 2:
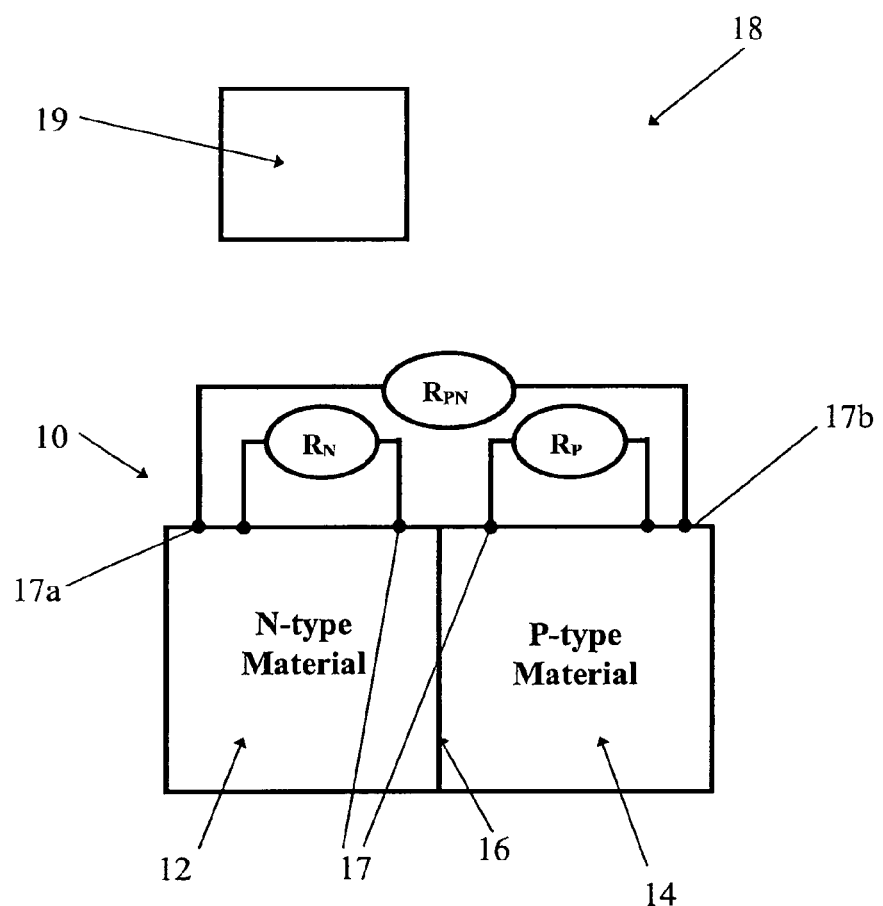
FIG. 2 illustrates a schematic representation of a sensor system including a sensor device in accordance with principles of the present disclosure.

FIG. 2 illustrates one embodiment of a sensor device 10 in accordance with principles of the present disclosure. The sensor device 10 includes a sensing element or p-n junction device 11 akin to a MOS sensing element, but formed by at least two discrete MOS materials. Namely, the sensing element 11 includes a first, n-type MOS material region 12 and a second, p-type MOS material region 14. A diffuse p-n junction 16 is established between the n-type region 12 and the p-type region 14 (e.g., the p-type and n-type semiconductive materials share a diffuse boundary). The n-type and p-type regions 12, 14 are formed immediately adjacent one another, and can contact one another at the p-n junction 16. Electrodes or other electrical lead-type bodies (identified generally at 17 in FIG. 2) are, or can be, selectively or permanently established at nodes within each of the regions 12, 14 (e.g., gold electrodes provided with a gold microspring array (now shown)). Electrical connections (e.g., wires) can be established between selected pairs of the so-established electrodes or nodes 17, with FIG. 2 illustrating three possible connections as measured resistances $R_{PP}$, $R_{NN}$, and $R_{PN}$. $R_{PP}$ represents a measured resistance between two nodes 17 only in the p-type region 12. $R_{NN}$ represents a measured resistance between two nodes only within the n-type region 14. $R_{PN}$ represents a measured resistance spanning both the p- and n-type regions 12, 14 (e.g., the electrodes 17a and 17b of FIG. 2). In one embodiment, a platform (not shown, but akin to the platform 4 of FIG. 1) supports the sensor element 11 and is maintained at a temperature optimized for the analyte with all of the data shown in this disclosure application being done at, for example, 300° C.

Gas Identification: If the p-type and n-type semiconductors 12, 14 show reverse conductivity changes in response to test gases due to the opposite charge carriers, the combination of a p-n array in the sensor device 10 can be used to reduce the resistance change, and thereby signal from specific analyte species.

The sensor device 10 can be provided as part of a sensor system 18 in accordance with principles of the present disclosure. The sensor system 18 can include components conventionally employed with MOS-type gas sensor systems, such as a housing (not shown) for directing a gas or other substance of interest across the sensing element 11, electronics for establishing and measuring conductivity at the desired connections (e.g., $R_{PP}$, $R_{NN}$, $R_{PN}$), and a controller 19 (e.g., a computer or other logic device) for transmitting and/or interpreting the measured conductivity signals. The controller 19 is further programmed to determine the presence and amount (e.g., in ppm or ppb) of one or more analytes (e.g., ambient gas) of interest based upon the measured conductivity signals.

The p-type material region 12 consists of a p-type MOS material that conducts with positive holes being the majority charge carrier. In the presence of an oxidizing gas, the p-type MOS material exhibits an increase in conductivity (or decrease in resistivity). An opposite effect is exhibited by the p-type MOS material in the presence of a reducing gas. In some embodiments, the p-type MOS material utilized for the p-type region 12 is CuO, although other p-type MOS materials can be employed.

The n-type material region 14 consists of a n-type MOS material in which the majority charge carriers are electrons. Upon interaction with an oxidizing gas, the n-type MOS material exhibits a decrease in conductivity (or increase in resistivity). An opposite effect is exhibited by the n-type MOS material in the presence of a reducing gas. In some embodiments, the n-type MOS material utilized for the n-type region 14 is $SnO_2$, $ZnO_2$, or $TiO_2$, although other n-type MOS materials can be employed.

Figure 3:
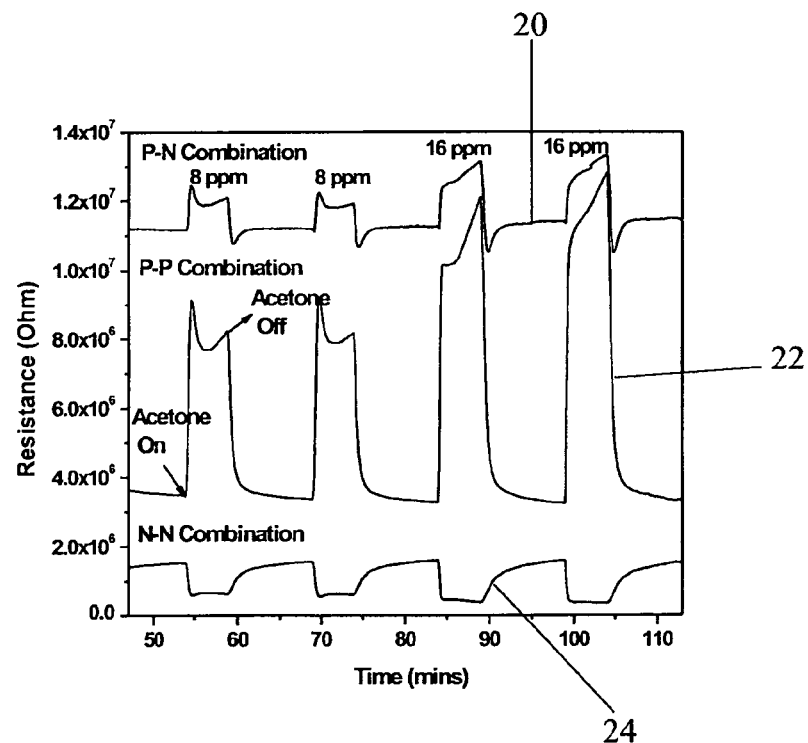
FIG. 3 is a graph illustrating response of a sensor device in accordance with principles of the present disclosure to varying concentrations of acetone.

The measured conductivities at the p-type region $R_{PP}$, at the n-type region $R_{NN}$, and across the p-n junction $R_{PN}$ can be evaluated to determine the presence and amount of a particular gas. For example, FIG. 3 illustrates response of a sensor device of the present disclosure (having p-type material of CuO and n-type material of $SnO_2$) to 10% $O_2$ and 8 ppm or 16 ppm acetone. The measured resistance across the p-n junction 16 (i.e., $R_{PN}$) is identified at 20, at the p-type region 12 (i.e., $R_{PP}$) is identified at 22, and at the n-type region 14 (i.e., $R_{NN}$) is identified at 24. FIG. 3 demonstrates that the response 20 to acetone decreases across the p-n junction 16, as compared to the p-type response 22 in the p-type region 12.

Figure 4:
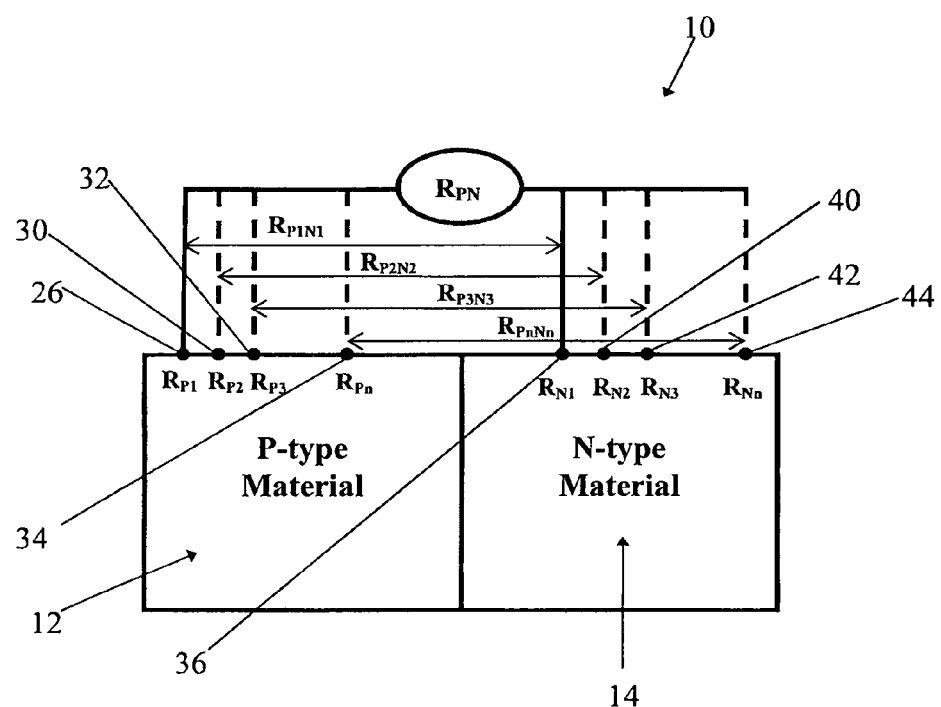
FIG. 4 illustrates a schematic representation of another sensor device in accordance with principles of the present disclosure.

The signal analysis in accordance with the present disclosure can assume various forms, and can include obtaining a multiplicity of p-n junction measurements at differing nodes within the p-type region and the n-type region. For example, FIG. 4 illustrates an alternative layout of leads or nodes (and corresponding electrical connections or wires) along the sensor device 10 and will help explain further the basis of the analyte identification based on a concept of cancellation. With a proper combination of the p-type material (e.g., CuO) in the p-type region 12 and n-type material (e.g., $SnO_2$) in the n-type region 14, using one of the lead wires from the electrodes or nodes at $R_{P1}$ 26, $R_{P2}$ 30, $R_{P3}$ 32, $R_{Pn}$ 34 in the p-type region 12 and other lead wires from the electrodes or nodes at $R_{N1}$ 36, $R_{N2}$ 40, $R_{N3}$ 42, $R_{Nn}$ 44 in the n-type region 14, the analyte signal may diminish completely and may be treated as null response for the particular analyte. Thus, different types of analyte molecules will have unique null response spacings. For example, a first analyte will have a null response spacing between $R_{P1}$ 26 and $R_{N1}$ 36, a second (different) analyte will have a null response spacing between $R_{P2}$ 30 and $R_{N2}$ 40, etc.

With the above in mind, the null response data can be used as a "fingerprint" signature that is unique to a specific analyte. Thus, in a blind study, systems of the present disclosure can elucidate the identity of analytes using this "fingerprint" signature technique. For example, the controller 19 (FIG. 2) can be programmed to include a database of various analytes and their corresponding, previously-determined null response data; the controller 19 can compare the conductivity information (e.g., statistical comparison of null spacing data) for an unknown analyte being tested with the database to identify the unknown analyte.

Figure 5:
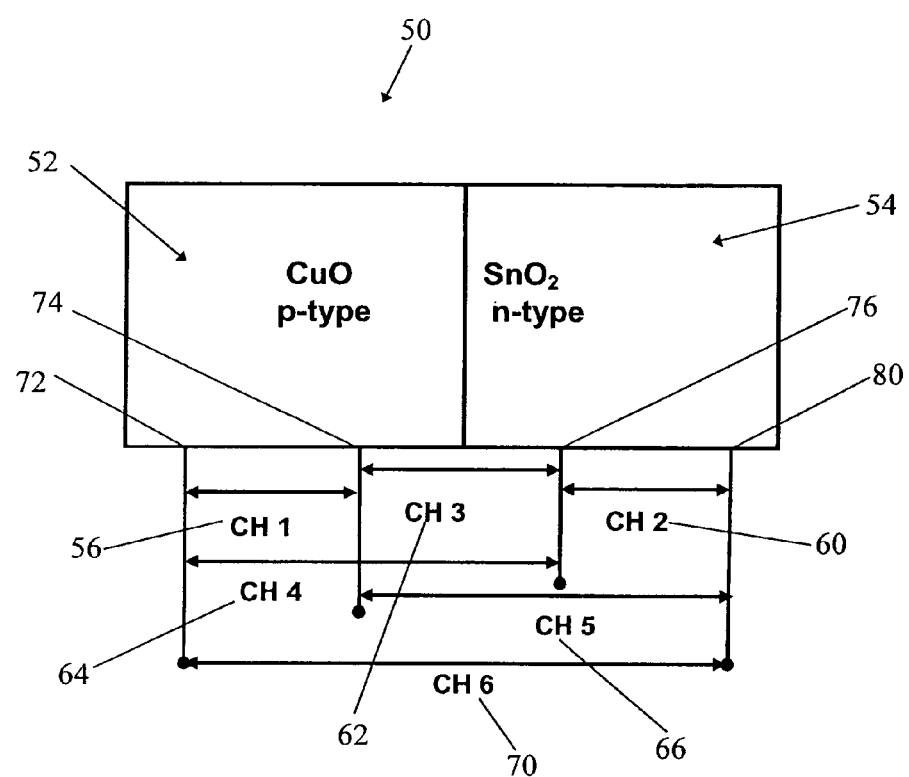
FIG. 5 illustrates a schematic representation of another sensor device in accordance with principles of the present disclosure.
Figure 6:
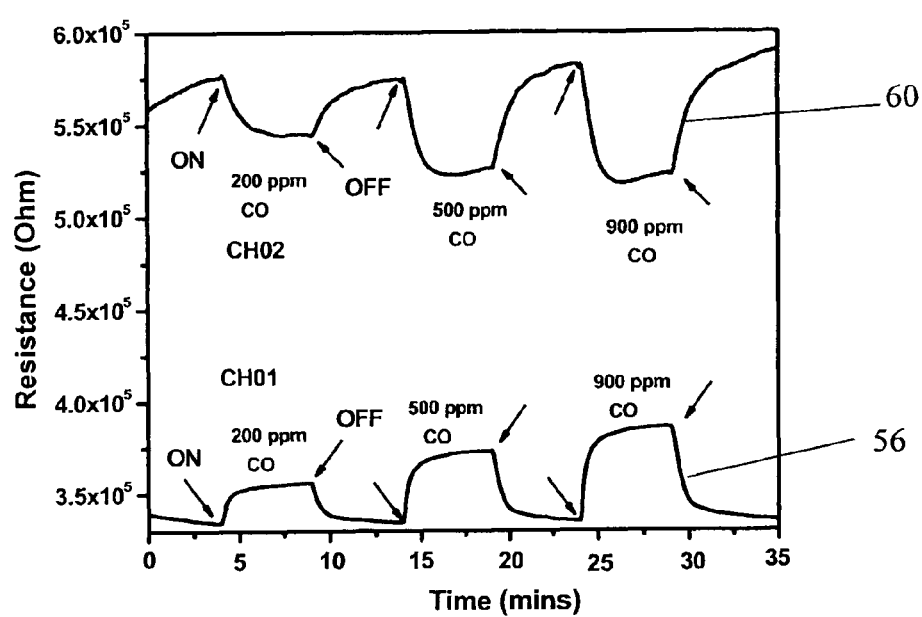
FIG. 6 is a graph illustrating response of the sensor device of FIG. 5 to varying concentrations of CO at two channels identified herein.
Figure 7:
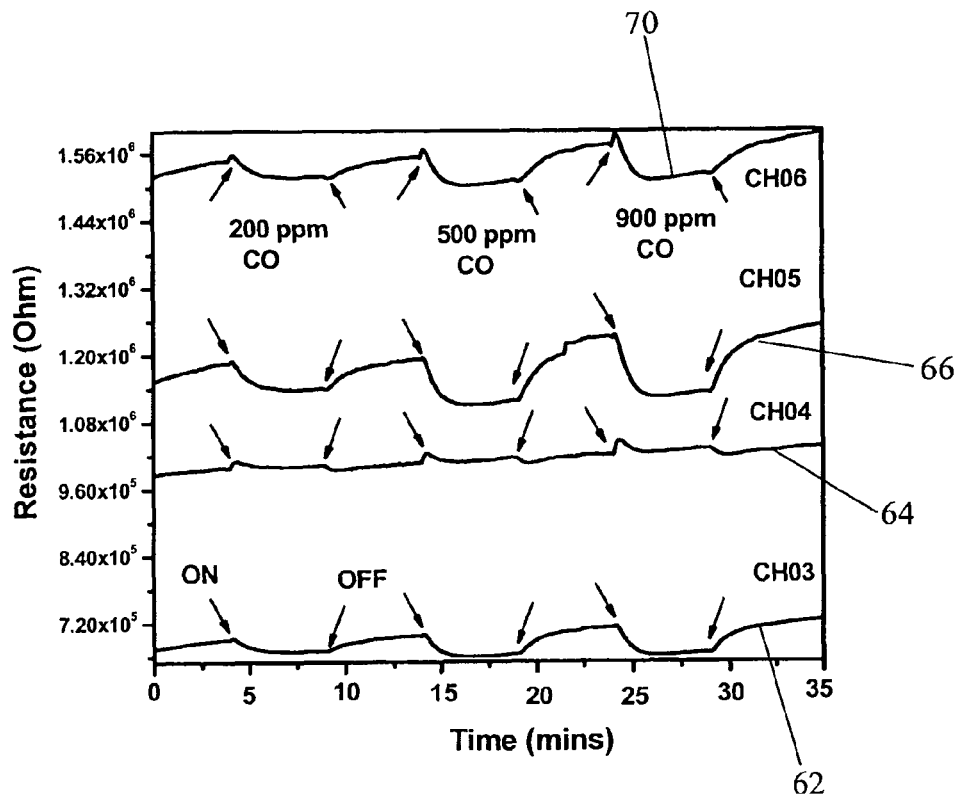
FIG. 7 is a graph illustrating response of the sensor device of FIG. 5 to varying concentrations of CO at channels identified herein, including a cancellation signal for CH 04 in accordance with one embodiment of an apparatus illustrating principles of the present disclosure.

As an example for the case of CO, FIG. 5 shows another sensor device 50 which is an array of p-type CuO material 52 and n-type $SnO_2$ material 54. Channels 1-6 ("CH 1"-"CH 6") 56, 60, 62, 64, 66, 70 are illustrated between various electrodes wires from the electrodes or nodes 72, 74, 76, 80. The sensor device 50 was exposed to a background gas of air mixed with CO at different concentration levels (200 ppm CO, 500 ppm CO, and 900 ppm CO). FIG. 6 illustrates graphs of sensed resistances at Channels 1 and 2 56, 60 and FIG. 7 illustrates graphs of Channels 3, 4, 5 and 6 62, 64, 66, 70 at the three CO concentration levels. Channel 1 56 measures resistance in the p-type region 52 and Channel 2 60 measures resistance in the n-type region 54. Channels 1 and 2 56, 60 illustrate expected resistance increases and decreases, respectively, (as measured from the ON points to the respective OFF points) in the presence of CO.

With continued reference to FIG. 7, the response to CO is nullified as illustrated by Channel 4 64. It is contemplated that the CO is nullified along Channel 4 64 because the signal through the n-type material 54 cancels the signal through the p-type material 52 over the distance between the electrode wires 72 in the p-type material 52 and the electrode 76 in the n-type material 54. Although Channel 5 (between the electrode 74 in the p-type material 52 and the electrode 80 in the n-type material 54) is approximately the same distance as Channel 4, the path of Channel 5 travels through more of the n-type material 54 relative to the path of Channel 4.

It is contemplated that the sensor systems described herein can be made to be sensitive to one analyte and discriminate against another analyte. Sensitivity may also be modulated by changing the nature of the metal oxide. Such sensor arrays containing p and n type material with an array of wires (e.g., microspring electrodes) are expected to find applications in industrial, consumer and biomedical applications.

Although the present disclosure has been described with reference to preferred embodiments, workers skilled in the art will recognize that changes can be made in form and detail without departing from the spirit and scope of the present disclosure.

What is claimed is:

1. A sensor system comprising:
   a sensing element including:
      a p-type MOS material, and
      an n-type MOS material discrete from the p-type MOS material and contacting the p-type MOS material at a diffuse p-n junction;
   a plurality of electrode wires, including a first electrode wire connecting spaced electrodes in the p-type MOS material, a second electrode wire connecting spaced electrodes in the n-type MOS material, and a third electrode wire connecting an electrode in the p-type MOS material and an electrode in the n-type MOS material; and
   a controller programmed to determine a measured resistance across each of the first, second, and third electrode wires when the sensing element is exposed to a sample gas, estimate a null point from the measured resistances, and identify an analyte in the sample gas based on a statistical comparison of the measured resistances with a stored calibration database.

2. The sensor system of claim 1, wherein the p-type MOS material is CuO.

3. The sensor system of claim 1, wherein the n-type MOS material is selected from the group consisting of $SnO_2$, $ZnO_2$ and $TiO_2$.

4. The sensor system of claim 1, further comprising a microspring array establishing the electrodes along the p-type MOS material and the n-type MOS material.

5. The sensor system of claim 1, wherein the controller is further programmed to identify a specific gas from a sample containing a mixture of gases based upon the comparison.

6. The sensor system of claim 1, wherein the controller is further programmed to determine a desired distance between the electrodes of the third electrode wire based upon a sample gas.

7. The sensor system of claim 1, wherein a length of at least the third electrode wire is selected to effect a resistance in the third electrode wire.

8. The sensor system of claim 7, wherein a length of first electrode wire and a length of the second electrode wire are selected to effect a resistance in the first electrode wire and a resistance in the second electrode wire.

9. The sensor system of claim 1, wherein a distance between the electrodes of the third electrode wire is variable so as to obtain measured resistances across differing amounts of the p-type and n-type MOS materials.

10. The sensor system of claim 1, wherein the sensing element is provided as part of a sensor device further including a plurality of first available electrodes each contacting the p-type MOS material at discrete locations and a plurality of second available electrodes each contacting the n-type MOS material at discrete locations, and further wherein the sensor device is configured to selectively establish the third electrode wire between a selected one of the first available electrodes and a selected one of the second available electrodes.

11. The sensor system of claim 10, wherein the sensor system is configured to obtain measured resistances at a plurality of different pairings of one of the first available electrodes and one of the second available electrodes.

12. The sensor system of claim 10, wherein the sensor device is configured to selectively establish the first electrode wire between different ones of the first available electrodes.

13. The sensor system of claim 12, wherein the sensor device is configured to selectively establish the second electrode wire between different ones of the second available electrodes.

14. The sensor system of claim 10, wherein the p-type MOS material is arranged adjacent the n-type material such that the sensing element is defined by opposing, first and second sides, the first side established by an edge of the p-type MOS material opposite the p-n junction and the second side established by an edge of the n-type MOS material opposite the p-n junction, and further wherein a length direction of the sensing element is defined from the first end to the second end, and even further wherein at least two of the first available electrodes are spaced from one another in the length direction.

15. The sensor system of claim 14, wherein at least two of the second available electrodes are spaced from one another in the length direction.

16. The sensor system of claim 14, wherein the sensor device is configured to selectively connect the third electrode wire to different ones of the first and second available electrodes thereby including different amounts of the MOS materials in the length direction.

17. The sensor system of claim 16, wherein the sensor device is configured to establish differing, first and second arrangements of the third electrode wire, the first arrangement encompassing a distance along the p-type MOS material in the length direction that differs from a distance along the p-type MOS material in the length direction encompassed by the second arrangement.

* * * * *